US011802298B2

(12) United States Patent
Xu et al.

(10) Patent No.: US 11,802,298 B2
(45) Date of Patent: Oct. 31, 2023

(54) DECANEDIOIC ACID PRODUCED BY MICROBIAL FERMENTATION PROCESS AND PREPARATION METHOD THEREOF

(71) Applicants: Cathay Biotech Inc., Shanghai (CN); CIBT America Inc., Newark, DE (US)

(72) Inventors: Min Xu, Shanghai (CN); Yingli Hao, Shanghai (CN); Chen Yang, Shanghai (CN); Naiqiang Li, Shanghai (CN); Xiucai Liu, Shanghai (CN)

(73) Assignees: Cathay Biotech Inc., Shanghai (CN); CIBT America Inc., Newark, DE (US)

( * ) Notice: Subject to any disclaimer, the term of this patent is extended or adjusted under 35 U.S.C. 154(b) by 429 days.

(21) Appl. No.: 17/082,124

(22) Filed: Oct. 28, 2020

(65) Prior Publication Data

US 2021/0040517 A1 Feb. 11, 2021

Related U.S. Application Data

(63) Continuation of application No. 16/049,119, filed on Jul. 30, 2018, now Pat. No. 10,851,394.

(30) Foreign Application Priority Data

Aug. 2, 2017 (CN) .......................... 201710653289.0

(51) Int. Cl.
| | | |
|---|---|---|
| C12P 7/64 | (2022.01) | |
| C12P 7/6409 | (2022.01) | |
| C08G 69/26 | (2006.01) | |
| C12P 7/44 | (2006.01) | |
| C08G 63/16 | (2006.01) | |
| C07C 55/20 | (2006.01) | |

(52) U.S. Cl.
CPC ............ *C12P 7/6409* (2013.01); *C07C 55/20* (2013.01); *C08G 63/16* (2013.01); *C08G 69/26* (2013.01); *C12P 7/44* (2013.01)

(58) Field of Classification Search
CPC .............. C12P 7/44; C07C 51/42; C12N 1/16
See application file for complete search history.

(56) References Cited

U.S. PATENT DOCUMENTS

| 3,896,011 A | 7/1975 | Isoya et al. |
| 2014/0228586 A1 | 8/2014 | Beardslee et al. |
| 2015/0044739 A1 | 2/2015 | Liu et al. |

FOREIGN PATENT DOCUMENTS

| CN | 101210071 A | 7/2008 | |
| CN | 101985416 A | 3/2011 | |
| CN | 102839133 A | 12/2012 | |
| CN | 104591998 A | 5/2015 | |
| CN | 104844440 A | 8/2015 | |
| EP | 3205687 A1 | 8/2017 | |
| GB | 945174 A | 12/1963 | |
| WO | 2001021572 A1 | 3/2001 | |
| WO | WO 2016030480 | * | 3/2016 |
| WO | 2016056340 A1 | 4/2016 | |

OTHER PUBLICATIONS

Kind et al From zero to hero—Production of bio-based nylon from renewable resources using engineered Corynebacterium glutamicum, Metabolic Engineering 25 (2014) 113-123, published online on May 2014.*
European Search Report for EP Application No. 18186235.0 dated May 22, 2019.
Shaohua, O., "Progress in the Preparation and Application of Sebacic Acid"; Chemical Inermediate (2010); 4 pgs.
Shuchen, L. et al., "Metabolism and β-Oxidation of Alkane-Utilizing Candida Tropicalis"; Acta Microbiologica Sinica (2002); vol. 42:1; 5 pgs.
Japu, C. et al., "Copolyesters Made from 1,4-butanediol, Sebacic Acid and D-Glucose by Melt and Enzymatic Polycondensation"; Biomacromolecules (2015); 47 pgs.
Du C. et al., "Succonic Acid Production from Wheat Using a Biorefining Strategy"; Appl Microbiol. Biotechnol (2007); vol. 76, pp. 1263-1270.

* cited by examiner

*Primary Examiner* — Gregory Listvoyb
(74) *Attorney, Agent, or Firm* — Fox Rothschild LLP

(57) ABSTRACT

The present invention provides a decanedioic acid produced by microbial fermentation process, in which the content of C10 aliphatic acid and C10 hydroxy aliphatic acid is maintained at a very low level. The present invention also provides a preparation method of the decanedioic acid and a polymer prepared by using the decanedioic acid as monomer. The decanedioic acid provided by the present invention is prepared by microbial fermentation process. The decanedioic acid product which is produced through the processes of microbial fermentation and separation has a higher purity, a higher thermal stability, and a lower impurity content. The decanedioic acid provided by the present invention could satisfy the requirements of high grade product of polyamide or polyester to produce polymer with excellent qualities. The preparation method of the decanedioic acid provided by the present invention which has many advantages of mild reaction conditions, environmental friendliness, high yield, and good product quality, may replace the chemical method to be used in industrial scale production of the decanedioic acid.

19 Claims, No Drawings

DECANEDIOIC ACID PRODUCED BY MICROBIAL FERMENTATION PROCESS AND PREPARATION METHOD THEREOF

TECHNICAL FIELD

The present invention relates to the field of microbial fermentation, in particular to a decanedioic acid produced by microbial fermentation process and a method of preparation thereof.

BACKGROUND ART

As one of widely used industrial chemicals, decanedioic acid has extensive application in producing polyamide engineering plastics, e.g. nylon 1010 and nylon 610, and also may used for heat-resistant lubricant, curing agent of epoxy resin, synthesized lubricating grease and artificial flavor, cold-resistant plasticizer, etc.

Presently, the decanedioic acid in industrial production and application is prepared by chemical method using castor oil as a material. The method mainly includes: producing sodium ricinoleate by hydrolysis of castor oil, followed by obtaining ricinoleic acid; heating the ricinoleic acid in the presence of an alkali and phenol to yield disodium sebacate through pyrolysis reaction; and then obtaining the decanedioic acid after processing steps of heating, acidizing, decolorizing and crystallizing. However, the preparation method of decanedioic acid by catalytic pyrolysis of castor oil greatly restricts the development of producing decanedioic acid in chemical method, because of complex production process, high reaction temperature of 250 to 270° C. and environmental pollution resulted by the toxic material of phenol or o-cresol.

Biological method for preparing decanedioic acid has characteristics of simple production process and less environmental pollution. People has made a lot of studies on the biological method, especially during the 70's and 80's. Zhihua Yu of Institute of Microbiology, Chinese Academy of Sciences, obtained an excellent bacterial strain by mutagenesis-selection, and optimized the fermentation conditions of producing decanedioic acid using the strain. The fermentation was performed in a 16 L-fermentor, the volumetric productivity of decanedioic acid in the fermentation broth reached at more than 71 g/L, and the decanedioic acid was obtained by aqueous crystallization with a purity of over 99.6% and a yield of 85%. Zutong Liu et al. selected a bacterial strain that could be used in producing decanedioic acid with a concentration of 2.9%. A team at Shenyang Institute of Applied Ecology, Chinese Academy of Sciences, selected *Candida lipolytica* which was used in producing decanedioic acid, with a productivity of 30-40 g/L and a reactant conversion of 43%-55%.

It is difficult to obtain decanedioic acid product prepared by biological method with lower impurity content for the reason that plenty of impurities are existed and not easy to be removed. The existence of impurities has great influence on the subsequent application of the decanedioic acid, for example, it is hard to obtain polyamide product with higher quality and performance using the above-mentioned decanedioic acid as material in polymerization. Current studies are mostly focused on the fermentation technology. Systematical researches on purification process of the fermentation broth has not been made, neither do the researches on the influence on the product properties exerted by impurities produced in the process of fermentation such as aliphatic acid comprising 10 carbons and hydroxy aliphatic acid comprising 10 carbons. Therefore, decanedioic acid product prepared by biological method with lower impurity content and higher quality is badly needed.

SUMMARY OF THE INVENTION

An object of the present invention is to provide a decanedioic acid produced by microbial fermentation process, with lower impurity content and higher quality.

Another object of the present invention is to provide a preparation method of the above-mentioned decanedioic acid.

Another object of the present invention is to provide a polymer product comprising the decanedioic acid produced by microbial fermentation process as monomer.

In the decanedioic acid produced by microbial fermentation process according to the present invention, the content of aliphatic acid comprising 10 carbons (C10 aliphatic acid) impurity is less than 200 ppm, preferably less than 50 ppm, and the content of hydroxy aliphatic acid comprising 10 carbons (C10 hydroxy aliphatic acid) impurity is less than 300 ppm, preferably less than 100 ppm. The impurity content of C10 aliphatic acid and C10 hydroxy aliphatic acid may be maintained at an extremely low level in the decanedioic acid produced by microbial fermentation process of the present invention. The present inventor have found that the obtained decanedioic acid product has a higher quality, especially in the preparation of polymer, such as polyamide and polyester, and the properties of the polymer products may be greatly improved.

Furthermore, the thermal stability of the decanedioic acid produced by microbial fermentation process provided according to the present invention is more than 90%, preferably more than or equal to 95%, more preferably more than or equal to 97%.

Common impurities such as sugar, nitrogen and unsaturated compounds in the decanedioic acid product may conduct chemical reactions in the presence of oxygen at high temperature, so the color of the decanedioic acid product may easily turn yellow, and this phenomenon is called thermal stability. The test of thermal stability includes the following steps: heating the product until melted, introducing a certain amount of oxygen, staying some time for the chemical reactions proceeding, testing the light transmittance at 400-600 nm wavelength of the final product, and calculating the relative value of the test result to the light transmittance of the decanedioic acid which does not subjected to chemical reactions in the presence of oxygen. Little change of light transmittance values represents good thermal stability of decanedioic acid product. According to the present invention, the thermal stability of the decanedioic acid product is greatly enhanced.

The preparation method of the decanedioic acid according to any one of the above-mentioned technical solutions of the present invention comprises: culturing *Candida tropicalis* to prepare a seed first; inoculating the obtained seed with fermentation medium subsequently; starting the fermentation process to produce fermentation broth by adding decane; and purifying the obtained fermentation broth to give the decanedioic acid.

According to the preparation method of the present invention, *Candida tropicalis* CAT N145 with a conservation number CCTCC M2011192 is preferably used. The biological and genetic characteristics of the strain are described in Chinese Patent application CN 102839133A with a publication date of Dec. 26, 2012. By using the strain in the process of producing decanedioic acid, the conversion rate of decane to decanedioic acid may be more than 80% by weight, and the productivity of decanedioic acid may be more than 100 g/L.

According to the preparation method of the present invention, common types of seed medium in the microbial fermentation field may be used in the process of seed culturing, for example, carbon source, nitrogen source, inorganic salt, nutrition factor, etc. Moreover, the carbon source comprises but not limited to glucose, maltose, sucrose, etc. The nitrogen source comprises but not limited to yeast extract, corn steep liquor, urea, ammonium sulfate, potassium nitrate, etc. The inorganic salt comprises but not limited to potassium nitrate, potassium phosphate monobasic, sodium chloride, ferrous sulfate, zinc sulfate, etc. Nutrition factor comprises but not limited to vitamin C, vitamin B1, biotin, etc. The seed medium may preferably comprise the following ingredients: 15-30 g/L sucrose, 2-10 g/L corn steep liquor, 1-8 g/L yeast extract, 4-12 g/L potassium phosphate monobasic, and 1-4 g/L urea. The temperature may be from 28° C. to 30° C. in the process of seed culturing which may be considered to be finished, as the growth rate of the seed proceeds to logarithmic phase. Then, the seed obtained is inoculated with fermentation medium to carry out the following fermentation process, and the inoculation amount may be from 5% to 25% (v/v).

According to the preparation method of the present invention, the fermentation medium may comprise the following ingredients: 0-50 g/L glucose, 1-10 g/L potassium nitrate, 2-10 g/L corn steep liquor, 1-8 g/L yeast extract, 1-10 g/L potassium phosphate monobasic, and 1-4 g/L ammonium sulfate.

The fermentation medium preferably may comprise the following ingredients: 25-40 g/L glucose, 1.2-2.5 g/L potassium nitrate, 2-5 g/L corn steep liquor, 1-3 g/L yeast extract, 1.8-3.5 g/L potassium phosphate monobasic, and 1.2-2 g/L ammonium sulfate.

The growth rate of the microorganism and the produce rate of decanedioic acid and other byproducts in the process of microbial transformation, especially the produce rate of C10 aliphatic acid and C10 hydroxy aliphatic acid, could be better controlled by adjusting the content of glucose, ammonium sulfate, potassium nitrate, and potassium phosphate monobasic in the fermentation medium. Therefore, the content of C10 aliphatic acid and C10 hydroxy aliphatic acid impurities may be effectively reduced, accordingly the subsequent purifying process may be simplified and the impurity content of the final decanedioic acid product may also be reduced.

According to the preparation method of the present invention, the seed obtained from the process of seed culture is inoculated with fermentation medium for bacterial culture. When OD 620 of the fermentation medium reaches more than 0.5 with a dilution of 1:30, the decane is added to conduct the fermentation process. During the fermentation process, OD 620 may be maintained at 0.3-0.8, more preferably at 0.4-0.7, further preferably at 0.4-0.5. Through controlling the bacterial concentration, the accumulation of the C10 aliphatic acid and C10 hydroxy aliphatic acid may be restrained and the conversion of decane may be promoted.

According to the preparation method of the present invention, the pH value may be maintained at 5.0-8.0 in the fermentation process. When the pH value is less than 5.0, the C10 aliphatic acid and C10 hydroxy aliphatic acid may be easily accumulated in the fermentation system, and when the pH value is more than 8.0, the yield of the decanedioic acid may be very low.

According to the preparation method of the present invention, the relative dissolved oxygen may be maintained at more than 10% (v/v), preferably at 10%-70%, more preferably at 40%-70%, in the fermentation process. The relative dissolved oxygen may be controlled by adjusting the stirring rate and air ventilation rate during the process of microbial transformation. Generally, the air ventilation rate may be maintained at 0.1-0.8 VVM, and the stirring rate may be adjusted according to production scale.

According to the preparation method of the present invention, the content of decane in the fermentation system may be controlled at more than or equal to 1% (v/v) by feeding the decane in continuous way or in batch way during the process of microbial transformation. The content of the decane in the obtained fermentation broth may be controlled at less than or equal to 0.5% (v/v) when the process of fermentation is terminated.

According to the preparation method of the present invention, other process parameters of the fermentation, e.g., temperature and pressure, may be common and well known in the art, or may be appropriately adjusted by a person skilled in the art according to other process conditions. In the fermentation process of the present invention, for example, the temperature may be maintained at 28° C.-32° C., and the fermentor pressure may be controlled at 0.03 MPa-0.1 MPa.

According to the preparation method of the present invention, the purifying process of the fermentation broth comprises the following steps:

S1: removing impurities by one or more separation processes consisting of membrane filtration, plate and frame filtration, and centrifugation to obtain decanedioic acid crude product;

S2: purifying the obtained decanedioic acid crude product by one or more crystallization processes to obtain decanedioic acid crystal; and S3: washing, drying the decanedioic acid crystal to give the decanedioic acid.

Step S1 is mainly to remove bacterium, residual hydrocarbon and metabolite impurities which may effect the downstream polymerization, from the fermentation broth to obtain the crude decanedioic acid. More than half of C10 aliphatic acid and C10 hydroxy aliphatic acid can be removed through step S1. Preferable example of the separation process is membrane filtration, and conventional microfiltration membrane or ultrafiltration membrane may be used. The operating temperature of the membrane filtration may be generally from 50° C. to 80° C., and the feed pressure into membrane and the discharge pressure out of membrane may be adjusted according to the components of the decanedioic acid crude product. The centrifugation may be generally conducted at the temperature of 70° C. to 80° C., and the rotational speed may be from 2000 rpm to 4000 rpm according to the quantity of the crude product to be separated.

Step S2 is mainly to purify the decanedioic acid crude product by crystallization, so as to further lower the content of C10 aliphatic acid and C10 hydroxy aliphatic acid. Water and/or other solvent may be used for the crystallization, and the other solvent may be selected from ethanol, acetic acid, ethyl acetate, and butyl acetate.

The crystallization process using water as solvent may generally comprise: mixing the decanedioic acid crude product with a certain amount of water to obtain a mixture with a 5%-10% (w/v) decanedioic acid content; heating the mixture to a temperature of 95° C.-110° C. gradually, followed by cooling down to 25° C.-30° C. to crystallize; and obtaining the crystal through centrifugation or plate and frame filtration.

Furthermore, acetic acid may be used as solvent in crystallization process, and the mass ratio of the decanedioic acid crude product to acetic acid may be 1/2 to 1/4, preferably 1/2.5 to 1/3.5. The crystallization process may comprise: heating the solution of the decanedioic acid crude product in acetic acid to a temperature of 90° C.-95° C., then cooling down to 20° C.-30° C. to crystallize. The content of acetic acid in the decanedioic acid crystal obtained may be maintained at less than 500 ppm, preferably less than 300 ppm.

Step S3 is mainly to wash and dry the purified decanedioic acid crystal to obtain the final product.

The present invention also provides a decanedioic acid produced by microbial fermentation process, in which the content of C10 aliphatic acid impurity may be less than 200 ppm, preferably less than 50 ppm, the content of C10 hydroxy aliphatic acid impurity may be less than 300 ppm, preferably less than 100 ppm, the content of acetic acid impurity may be less than 500 ppm, preferably less than 300 ppm; and/or the thermal stability is more than 90%, preferably more than or equal to 95%, more preferably more than or equal to 97%.

The present invention also provides a polymer prepared by using the decanedioic acid according to any one of the above-mentioned technical solutions as monomer.

The polymer may be any known polymer or modified polymer comprising decanedioic acid as a polymerization monomer, and may be any molecular weight and obtained by any polymerization process. Preferred polymer may be polyamide or polyester. More preferred polymer may be polyamide polymerized by the said decanedioic acid and aliphatic amine comprising 5 to 12 carbons. The aliphatic amine includes but not limited to pentamethylene diamine, hexamethylene diamine, decamethylene diamine, etc.

The decanedioic acid provided by the present invention is prepared by microbial fermentation process. The decanedioic acid product which is produced through the processes of microbial fermentation and separation has a higher purity, a higher thermal stability, and a lower impurity content, especially a lower content of C10 aliphatic acid and C10 hydroxy aliphatic acid that are common impurities in the preparation of decanedioic acid by biological method. The decanedioic acid product with high purity and low impurity content could satisfy the requirements of high grade product of polyamide or polyester to produce polymer with excellent qualities. Furthermore, the preparation method of the decanedioic acid provided by the present invention which has many advantages of mild reaction conditions, environmental friendliness, high yield, and good product quality, may replace the chemical method to be used in industrial scale production of the decanedioic acid.

DETAILED DESCRIPTION

In order to make the purpose, technical solutions and advantages of the present invention more clear, the technical solutions of the exemplary examples of the present invention will be further described below.

Example 1

*Candida tropicalis* CAT N145 with a conservation number CCTCC M2011192 was inoculated with seed medium to conduct the process of seed culture at 30° C. As the growth rate of the seed proceeded to the logarithmic phase, the seed liquid obtained was inoculated with fermentation medium to carry out the fermentation process, with the inoculation amount of 10% (v/v). In the process of fermentation, the temperature was 30° C., the pH value was maintained at 5.0-8.0, the air ventilation rate was controlled at 0.5 VVM, the fermentor pressure was controlled at 0.05 MPa, and the relative dissolved oxygen was maintained at 30%.

After the seed was inoculated into the fermentor, bacterium began to grow and multiply. When OD 620 of the fermentation medium reached more than 0.5 (with a dilution of 1:30), decane was added to conduct the microbial transformation process. The content of decane in the fermentation system was controlled at more than or equal to 1% (v/v) during the process of transformation. 24 hours before the end of the fermentation, the addition of decane was ended. Until the residual decane in the system all converted, the fermentation was terminated. The content of C10 aliphatic acid and C10 hydroxy aliphatic acid in the fermentation broth obtained was measured using gas chromatography.

The seed medium comprised:
20 g/L sucrose; 10 g/L corn steep liquor; 3 g/L yeast extract; 6 g/L potassium phosphate monobasic; and 3 g/L urea.

The fermentation medium comprised:
ammonium sulfate, potassium nitrate, and potassium phosphate monobasic with various concentrations shown in Table 1, and other ingredients: 50 g/L glucose; 3 g/L corn steep liquor; and 1 g/L yeast extract.

TABLE 1

| Initial Concentration | 1#<br>3.2 g/L Ammonium Sulfate; 3.4 g/L Potassium Nitrate; 5 g/L Potassium Phosphate Monobasic. | 2#<br>1.6 g/L Ammonium Sulfate; 1.7 g/L Potassium Nitrate; 2.5 g/L Potassium Phosphate Monobasic. | 3#<br>0.96 g/L Ammonium Sulfate; 1.02 g/L Potassium Nitrate; 1.5 g/L Potassium Phosphate Monobasic. | 4#<br>1.28 g/L Ammonium Sulfate; 1.36 g/L Potassium Nitrate; 2 g/L Potassium Phosphate Monobasic. |
|---|---|---|---|---|
| Content of C10 Hydroxy Aliphatic Acid in Fermentation Broth (mass ratio, compared to decanedioic acid) | 1.52% | 0.76% | 1.43% | 0.87% |
| Content of C10 Aliphatic Acid in Fermentation Broth (mass ratio, compared to decanedioic acid) | 0.70% | 0.49% | 1.18% | 0.55% |

TABLE 1-continued

|  | 1# | 2# | 3# | 4# |
|---|---|---|---|---|
| Initial Concentration | 3.2 g/L Ammonium Sulfate; 3.4 g/L Potassium Nitrate; 5 g/L Potassium Phosphate Monobasic. | 1.6 g/L Ammonium Sulfate; 1.7 g/L Potassium Nitrate; 2.5 g/L Potassium Phosphate Monobasic. | 0.96 g/L Ammonium Sulfate; 1.02 g/L Potassium Nitrate; 1.5 g/L Potassium Phosphate Monobasic. | 1.28 g/L Ammonium Sulfate; 1.36 g/L Potassium Nitrate; 2 g/L Potassium Phosphate Monobasic. |
| Average OD 620 during the process of transformation (with a dilution of 1:30) | 0.773 | 0.466 | 0.339 | 0.426 |

As can be seen from Table 1, the concentration of the bacterium during the process of conversion from decane to decanedioic acid could be adjusted by varying the concentrations of ammonium sulfate, potassium nitrate, and potassium phosphate monobasic in the fermentation medium, thereby the produce rate of decanedioic acid and other metabolites obtained by microbial transformation of substrate, especially the produce rate of C10 aliphatic acid and C10 hydroxy aliphatic acid could be controlled.

The fermentation process was conducted repeatedly in the condition of varying the initial concentration of glucose and using the same concentrations as solution 1# for other ingredients of the fermentation medium. The results are shown in Table 2.

TABLE 2

|  | 1# | 102# | 202# | 204# |
|---|---|---|---|---|
| Initial Concentration of Glucose | 50 g/L | 20 g/L | 30 g/L | 40 g/L |
| Concentration of C10 Hydroxy Aliphatic Acid in Fermentation Broth (mass ratio, compared to decanedioic acid) | 1.52% | 0.60% | 0.46% | 0.49% |

As can be seen from Table 2, the content of glucose in the fermentation medium also has an effect on the produce rate of metabolites, especially on the produce rate of C10 hydroxy aliphatic acid. When the concentration of glucose in the fermentation medium is from 25 g/L to 40 g/L, the content of C10 hydroxy aliphatic acid in the fermentation broth could be maintained at a lower level.

Example 2

Used Fermentation Medium Comprised:
50 g/L glucose; 3 g/L corn steep liquor; 1 g/L yeast extract; 3.2 g/L ammonium sulfate; 3.4 g/L potassium nitrate; and 5 g/L potassium phosphate monobasic.

The stirring rate and air ventilation rate was adjusted to control the relative dissolved oxygen in the process of microbial transformation, which had an effect on the content of C10 hydroxy aliphatic acid and C10 aliphatic acid in fermentation broth, and other steps and conditions were the same as Example 1. The results are shown in Table 3.

TABLE 3

|  | 102# | 103# | 104# | 203# |
|---|---|---|---|---|
| Relative Dissolved Oxygen | 10% | 70% | 50% | 90% |
| Fermentation Time (h) | 200 h | 182 h | 167 h | 171 h |
| Content of C10 Hydroxy Aliphatic Acid (mass ratio, compared to decanedioic acid) | 1.82% | 0.93% | 1.25% | 2.03% |
| Content of C10 Aliphatic Acid (mass ratio, compared to decanedioic acid) | 0.90% | 0.50% | 0.65% | 1.27% |

As can be seen from Table 3, the content of C10 hydroxy aliphatic acid and C10 aliphatic acid could be maintained at a lower level by controlling the relative dissolved oxygen below 90% in the process of microbial transformation, preferably from 10% to 70%, more preferably from 40% to 70%.

Example 3

The decanedioic acid fermentation broths 2# and 4# listed in Table 1 in Example 1 were processed by membrane filtration respectively. The pH value of fermentation broth was adjusted to 9.0-11.0, then the fermentation broth was heated to 70° C.-80° C., followed by filtering through microfiltration membrane with 0.05 μm pore size. Feed pump was used to maintain the feed pressure into membrane at about 0.15 to 0.2 MPa and the discharge pressure out of membrane at about 0.1 MPa. The C10 aliphatic acid and most of the hydroxyl acid were efficiently intercepted through the membrane filtration. The results are shown in Table 4.

TABLE 4

| Number | C10 Hydroxy Aliphatic Acid (compared to decanedioic acid) (ppm) | C10 Aliphatic Acid (compared to decanedioic acid) (ppm) | C10 Hydroxy Aliphatic Acid (compared to decanedioic acid) (ppm) | C10 Aliphatic Acid (compared to decanedioic acid) (ppm) |
|---|---|---|---|---|
|  | Content Before Membrane Filtration | | Content After Membrane Filtration | |
| Fermentation Broth 4# | 8724 | 5524 | 3925 | 828 |
| Fermentation Broth 2# | 7640 | 4987 | 3438 | 798 |

Example 4

The decanedioic acid fermentation broths 2# and 4# listed in Table 1 in Example 1 were heated to 70° C.-80° C. respectively, then processed by centrifugation to remove the C10 aliphatic acid and C10 hydroxyl aliphatic acid. The rotational speed of the centrifugation was 3000 rpm. The C10 aliphatic acid and some of the hydroxyl acid were efficiently removed through the centrifugation. The results are shown in Table 5.

TABLE 5

| Number | C10 Hydroxy Aliphatic Acid (compared to decanedioic acid) (ppm) | C10 Aliphatic Acid (compared to decanedioic acid) (ppm) | C10 Hydroxy Aliphatic Acid (compared to decanedioic acid) (ppm) | C10 Aliphatic Acid (compared to decanedioic acid) (ppm) |
|---|---|---|---|---|
|  | Content Before Centrifugation | | Content After Centrifugation | |
| Fermentation Broth 4# | 8724 | 5524 | 4362 | 1657 |
| Fermentation Broth 2# | 7640 | 4987 | 3972 | 1445 |

Example 5

Centrifuged fermentation broths 2# and 4# in Example 4 were diluted with 10 to 15 times deionized water respectively, followed by heating gradually to 100° C. to 105° C., then cooling down gradually to maintain the process of crystal growth to give decanedioic acid crystal crystallized by using water as solvent. The decanedioic acid crystal was processed by plate and frame filtration and dried to obtain decanedioic acid product. The contents of the C10 aliphatic acid and hydroxyl acids in the product are shown in Table 6.

TABLE 6

| Number | C10 Hydroxy Aliphatic Acid (compared to decanedioic acid) (ppm) | C10 Aliphatic Acid (compared to decanedioic acid) (ppm) | C10 Hydroxy Aliphatic Acid (compared to decanedioic acid) (ppm) | C10 Aliphatic Acid (compared to decanedioic acid) (ppm) |
|---|---|---|---|---|
|  | Content Before Crystallization | | Content After Crystallization | |
| Sample 4# | 4362 | 1657 | 2399 | 1242 |
| Sample 2# | 3972 | 1445 | 2264 | 1127 |

Example 6

The decanedioic acid products obtained through crystallization using water as solvent in Example 5 were marked as 4#-water and 2#-water respectively. Acetic acid was separately added to the samples 4#-water and 2#-water to conduct solvent crystallization, the mass ratio of decanedioic acid to acetic acid was maintained at 1/2-1/4. The obtained solutions were heated to 80° C.-100° C., and then cooled down to 20° C.-35° C. gradually to control the time of crystal growth. After precipitation of the crystal, liquid solid separation was carried out. The resulting solid was washed by solvent and water, and dried to give the product. The contents of impurities are shown in Table 7.

TABLE 7

| Number | C10 Hydroxy Aliphatic Acid (compared to decanedioic acid) (ppm) | C10 Aliphatic Acid (compared to decanedioic acid) (ppm) | C10 Hydroxy Aliphatic Acid (compared to decanedioic acid) (ppm) | C10 Aliphatic Acid (compared to decanedioic acid) (ppm) | Purity of Decanedioic Acid (%) Product |
|---|---|---|---|---|---|
|  | Content Before Crystallization | | Content After Crystallization | | |
| 4#-water | 2399 | 1242 | 285 | 50 | 99.72% |
| 2#-water | 2264 | 1127 | 272 | 46 | 99.85% |

Ethyl acetate was used instead of acetic acid to carry out the above-mentioned crystallization procedure. The contents of impurities in the resulting decanedioic acid product are shown in Table 8.

TABLE 8

| Number | C10 Hydroxy Aliphatic Acid (compared to decanedioic acid) (ppm) Content Before Crystallization | C10 Aliphatic Acid (compared to decanedioic acid) (ppm) | C10 Hydroxy Aliphatic Acid (compared to decanedioic acid) (ppm) Content After Crystallization | C10 Aliphatic Acid (compared to decanedioic acid) (ppm) | Purity of Decanedioic Acid (%) Product |
|---|---|---|---|---|---|
| 4#-water | 2399 | 1242 | 352 | 152 | 99.65% |
| 2#-water | 2264 | 1127 | 339 | 137 | 99.75% |

Example 7

Different batches of the decanedioic acid products obtained from the solvent crystallization were separately processed through same crystallization procedure using acetic acid as solvent in Example 6 to further reduce the content of impurities and enhance the product quality. The test results are shown in Table 9.

TABLE 9

| Batch Number | C10 Hydroxy Aliphatic Acid (compared to decanedioic acid) (ppm) | C10 Aliphatic Acid (compared to decanedioic acid) (ppm) |
|---|---|---|
| 1 | 48 | 13 |
| 2 | 52 | 5 |
| 3 | 54 | 16 |
| 4 | 36 | 11 |
| 5 | 30 | 14 |
| 6 | 27 | 10 |
| 7 | 50 | 14 |
| 8 | 36 | 11 |
| 9 | 54 | 16 |
| 10 | 89 | 19 |
| 11 | 64 | 9 |

The preparation process of PA 610 was as follows:

Step (1)

A 100 L-polymerizer was subjected to nitrogen replacement, followed by charging with 20 kg of purified water. 11 kg of hexamethylene diamine was added with stirring, and then 19 kg of decanedioic acid was added. A small amount of hexamethylene diamine and decanedioic acid was added to adjust pH value of the resulting solution to 8.2 (a test result of the solution diluted to 10% w/w), and nylon salt aqueous solution was obtained.

Step (2)

In nitrogen atmosphere, the polymerizer was heated gradually to a oil bath temperature of 280° C., and started to exhaust air when the pressure in the polymerizer rose to 1.73 MPa. Sodium pyrophosphate aqueous solution containing 90 g of titanium dioxide was added when the temperature in the polymerizer was 245° C. When the temperature in the polymerizer was 270° C., the polymerizer was vacuumized to a pressure of −0.08 MPa, followed by maintaining for 20 minutes to give nylon 610.

Step (3)

Nitrogen was introduced to the polymerizer until the pressure was 0.6 MPa. The melted product began to be extruded and granulated by pelletizer, followed by drying in vacuo at 100° C. for 24 hours and packing.

TABLE 10

Comparison of Decanedioic Acid (DC10) Products in Performance and Composition

| Sample | Water Content (%) | Melting Point (° C) | Content of DC10 (%) | Content of Ferric Salts (ppm) | Ash Content (ppm) | Thermal Stability | C10 Hydroxy Aliphatic Acid (ppm) | C10 Aliphatic Acid (ppm) | Yellow Index (YI) |
|---|---|---|---|---|---|---|---|---|---|
| Chemical Method | 0.06 | 129.9-134.1 | 99.58 | 1.8 | 223 | 90.85 | 82 | 121 | 3.49 |
| Biological Method | 0.02 | 130.1-134.4 | 99.83 | 1.3 | 31 | 97.32 | 69 | 17 | 0.67 |

Application Example

PA 610 was prepared according to below steps by using the decanedioic acid product of present invention and commercial decanedioic acid produced by conventional chemical method as material respectively. The performances of the decanedioic acid products and the PA 610 prepared are separately shown in the tables below.

TABLE 11

Comparison of PA 610 in Performance

| | Viscosity Number | Yellow Index | Appearance |
|---|---|---|---|
| PA 610 Prepared by Biological Method | 168 mL/g | −2 | White |
| PA 610 Prepared by Chemical Method | 156 mL/g | 3 | White |

As can be seen from the results of Tables 10 and 11, compared with the product prepared by chemical method, the decanedioic acid product of the present invention that is of higher qualities, especially in the respects of impurity content and thermal stability, is suitable for application of preparing polymer to improve the qualities and properties of the polymer. The decanedioic acid product and preparation method of the present invention make the decanedioic acid prepared by biological method more potential in application, which offers a possibility for replacing the decanedioic acid prepared by chemical method in industrial scale production.

Unless otherwise specified, the terms used in the present invention have the meanings as commonly understood by those skilled in the art.

While the present invention has been described with reference to the preferred embodiments thereof, it should be understood by those skilled in the art that various modifications, additions and substitutions may be made without departing from the true spirit and scope of the invention.

What is claimed is:

1. A method of preparing decanedioic acid, comprising:
culturing *Candida tropicalis* to obtain a seed culture;
inoculating the obtained seed culture with a fermentation medium;
starting a fermentation process to produce fermentation broth by adding decane; and
purifying the obtained fermentation broth to give the decanedioic acid;
wherein the fermentation medium comprises the following ingredients: 1-10 g/L potassium nitrate, 1-10 g/L potassium phosphate monobasic, and 1-4 g/L ammonium sulfate, and
wherein the content of aliphatic acid comprising 10 carbons is less than 200 ppm, and the content of hydroxy aliphatic acid comprising 10 carbons is less than 300 ppm.

2. The method according to claim 1, wherein the fermentation medium also comprises the following ingredients: 0-50 g/L glucose, 2-10 g/L corn steep liquor and 1-8 g/L yeast extract.

3. The method according to claim 1, wherein the fermentation medium comprises the following ingredients: 1.2-2.5 g/L potassium nitrate, 1.8-3.5 g/L potassium phosphate monobasic, and 1.2-2 g/L ammonium sulfate.

4. The method according to claim 1, wherein the decane is added when OD 620 of the fermentation medium with a dilution of 1:30 reaches more than 0.5.

5. The method according to claim 4, wherein the OD 620 of the fermentation medium with a dilution of 1:30 is maintained at 0.3-0.8 in the fermentation process.

6. The method according to claim 1, wherein relative dissolved oxygen is maintained at more than 10% (v/v).

7. The method according to claim 6, wherein the relative dissolved oxygen is maintained at 10% to 70% in the fermentation process.

8. The method according to claim 1, wherein pH value is maintained at 5.0-8.0 in the fermentation process.

9. The method according to claim 1, wherein the content of decane in fermentation system is maintained at more than or equal to 1% (v/v) by feeding the decane in a continuous way or in a batch way in the fermentation process, and wherein the content of decane in the obtained fermentation broth is maintained at less than or equal to 0.5% (v/v) when the fermentation process is terminated.

10. The method according to claim 1, wherein the *Candida tropicalis* is *Candida tropicalis* CAT N145.

11. The method according to claim 1, wherein purifying the obtained fermentation broth comprises the following steps:
S1: removing impurities by one or more separation processes consisting of membrane filtration, plate and frame filtration, and centrifugation to obtain decanedioic acid crude product;
S2: purifying the obtained decanedioic acid crude product by one or more crystallization processes to obtain decanedioic acid crystals; and
S3: washing and drying the decanedioic acid crystals to yield the decanedioic acid.

12. The method according to claim 11, wherein a crystallization solvent is used in the one or more crystallization processes in the step S2;
wherein the crystallization solvent is selected from the group consisting of water, ethanol, acetic acid, ethyl acetate, and butyl acetate.

13. The method according to claim 12, the crystallization process using water as solvent comprising: mixing the decanedioic acid crude product with a certain amount of water to obtain a mixture with a 5%-10% (w/v) decanedioic acid content; heating the mixture to a temperature of 95° C.-110° C., followed by cooling down to 25° C.-30° C. to crystallize; and obtaining the crystals through centrifugation or plate and frame filtration.

14. The method according to claim 12, the crystallization process using acetic acid as solvent comprising: heating the solution of the decanedioic acid crude product in acetic acid to a temperature of 90° C.-95° C., then cooling down to 20° C.-30° C. to crystallize;
wherein the mass ratio of the decanedioic acid crude product to acetic acid is 1/2 to 1/4.

15. The method according to claim 12, wherein the crystallization solvent is acetic acid, and the content of acetic acid in the obtained decanedioic acid crystals is maintained at less than 500 ppm.

16. A decanedioic acid product produced by the method according to claim 1.

17. The decanedioic acid product according to claim 16, wherein the thermal stability of the decanedioic acid is more than 90%.

18. A polymer prepared by using the decanedioic acid produced by the method according to claim 1 as monomer, wherein the polymer is selected from polyamide or polyester.

19. The polymer according to claim 18, wherein the polymer is polyamide polymerized by the decanedioic acid and aliphatic amine comprising 5 to 12 carbons, and wherein the aliphatic amine is selected from pentamethylene diamine, hexamethylene diamine, or decamethylene diamine.

* * * * *